United States Patent
Watanabe

(10) Patent No.: US 7,988,356 B2
(45) Date of Patent: Aug. 2, 2011

(54) RADIOGRAPHIC IMAGING APPARATUS AND METHOD

(75) Inventor: Tetsuo Watanabe, Utsunomiya (JP)

(73) Assignee: Canon Kabushiki Kaisha, Tokyo (JP)

(*) Notice: Subject to any disclaimer, the term of this patent is extended or adjusted under 35 U.S.C. 154(b) by 147 days.

(21) Appl. No.: 12/551,735

(22) Filed: Sep. 1, 2009

(65) Prior Publication Data

US 2010/0054419 A1    Mar. 4, 2010

(30) Foreign Application Priority Data

Sep. 2, 2008 (JP) ................. 2008-224648

(51) Int. Cl.
*H01J 31/49* (2006.01)
(52) U.S. Cl. .......................... 378/189; 378/91
(58) Field of Classification Search ............ 378/91, 378/114, 189
See application file for complete search history.

(56) References Cited

U.S. PATENT DOCUMENTS

| | | | | |
|---|---|---|---|---|
| 6,469,312 B2* | 10/2002 | Agano | ............... | 250/580 |
| 7,078,703 B2* | 7/2006 | Watanabe | ............... | 250/370.15 |
| 7,104,687 B2* | 9/2006 | Okamura et al. | ............... | 378/200 |
| 7,889,843 B2* | 2/2011 | Watanabe | ............... | 378/116 |

FOREIGN PATENT DOCUMENTS

| | | |
|---|---|---|
| JP | 2000-037374 A | 2/2000 |
| JP | 2005-000370 A | 1/2005 |

* cited by examiner

*Primary Examiner* — Jurie Yun
(74) *Attorney, Agent, or Firm* — Canon U.S.A., Inc., IP Division

(57) ABSTRACT

A cooling unit is provided in a storage section to locally cool a heat generating portion of an imaging device and to thereby reduce nonuniformity of the distribution of the temperature in the imaging device. Detectors detect a mount orientation of the imaging device, that is, whether the imaging device is mounted in landscape orientation or portrait orientation. Cooling portions of the cooling unit are selectively driven on the basis of the detection result.

11 Claims, 12 Drawing Sheets

RADIOGRAPHIC IMAGING APPARATUS AND METHOD

BACKGROUND OF THE INVENTION

1. Field of the Invention

The present invention relates to cooling of a radiographic imaging apparatus.

2. Description of the Related Art

Recent advances in digital technology have popularized methods for obtaining a high-quality radiographic image by converting a radiographic image into electrical signals, subjecting the objected electrical signals to image processing, and reproducing the electrical signals as a visual image on a CRT or the like. As such a method, a radiographic-image recording/reproducing system has been proposed. In the radiographic-image recording/reproducing system, a radiographic image is temporarily stored in a fluorescent substance, and a latent image is photoelectrically read out and output as a visual image by irradiation with excitation light such as laser light. Further, with recent advances in semiconductor process technology, a system for similarly taking a radiographic image with a semiconductor sensor has been developed.

Compared with a radiographic system of the related art using a photosensitive film, the above-described systems have an extremely wide dynamic range, and can obtain a radiographic image that is rarely affected by the change in irradiation amount. Also, these systems do not need chemical treatment, and can instantaneously obtain an output image, unlike the method using a photosensitive film.

FIG. 12 is a structural view of the above-described radiographic imaging system using a semiconductor sensor. Referring to FIG. 12, an imaging apparatus 2 mounted on an imaging table 1 incorporates a radiation detection sensor 3 having a detection surface on which a plurality of photoelectric conversion elements are arranged in a two-dimensional manner.

Radiation is emitted from a radiation generation unit 4 onto a subject S. The radiation passing through the subject S is converted into a visible image by the radiation detection sensor 3 via a fluorescent substance. Electric signals output from the radiation detection sensor 3 are red out by a control unit 5, are subjected to digital image processing, and are displayed as a radiographic image of the subject S on a monitor 6.

This radiographic imaging system allows instantaneous observation of the image, unlike the above-described radiographic-image recording/reproducing system that reads out an image by post-processing. In this imaging system, the imaging apparatus is mounted on the support unit dedicated to an imaging mode for, for example, a standing position or a lying position, and is selected as desired. The imaging device is fixed in a radiation room. Further, portable imaging apparatuses have recently been developed so as to be used when imaging needs to be performed in an arbitrary position.

Since such an imaging apparatus is an electronic apparatus, it includes multiple electronic components that are essential to digitalization, but have a problem of heat generation. It is necessary to efficiently radiate heat from the electronic components. Heat radiation is important not only in improving normal operation and durability of the electronic components that generate heat, but also in preventing the characteristic of the radiation detector from being changed by a rise in internal temperature of the imaging apparatus. Further, to ensure safety of the subject, there are regulations of the temperature of the surface of a portion of medical equipment the subject touches. Hence, it is necessary to limit the rise in temperature of the exterior of the imaging apparatus.

To this end, an imaging apparatus disclosed in Japanese Patent Laid-Open No. 2000-37374 is provided with a cooling mechanism that removes heat generated in the imaging apparatus by taking in air from a suction port and causing the air to flow around the imaging apparatus by an air cooling fan. Also, Japanese Patent Laid-Open No. 2005-370 proposes a cooling mechanism that switches a heat radiation path so that heat radiation can be effectively performed in accordance with the mounting manner, for example, a standing position or a lying position.

While the above-described imaging apparatus including the cooling mechanism has been used in the field of general still imaging, there is a demand to apply the imaging apparatuses to a movie taking apparatus because the imaging apparatus is smaller and lighter than an TV image pickup system of an X-ray image intensifier (II) type having an imaging area of a similar size.

Since continuous imaging is performed in movie taking, however, the amount of generated heat becomes larger than in still image taking of the related art. Moreover, since imaging is performed in various positions, it is necessary to consider the influence of the position of the imaging apparatus on heat generation.

It has also been proposed to use an imaging apparatus, which is detachable from a table, alone as a cassette type apparatus, unlike the stationary imaging apparatuses disclosed in Japanese Patent Laid-Open Nos. 2000-37374 and 2005-370. In this case, to improve cooling performance, as described above, it is necessary to mount a new cooling mechanism in the imaging apparatus. This reduces advantages of small size and light weight of the imaging apparatus. Accordingly, there is a plan for an imaging apparatus that can take a movie while being forcibly cooled from outside with a cooling unit provided in a support unit supporting the imaging apparatus.

SUMMARY OF THE INVENTION

The present invention provides a radiographic imaging apparatus that achieves high cooling efficiency in accordance with the position and posture of an imaging device that is detachably mounted in a support unit.

In order to achieve the above object, for example, a radiographic imaging apparatus of the present invention comprises the following arrangement.

The radiographic imaging apparatus includes an imaging unit configured to convert radiation into an electric signal; a support unit configured to support the imaging unit detachably; a cooling unit provided in the support unit, the cooling unit cooling the imaging unit; an information acquisition unit configured to acquire information about at least one of a position and a posture of the imaging unit; and a control unit configured to control driving of the cooling unit according to the acquired information.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

Preferred embodiments of the present invention will be described in detail in accordance with FIGS. 1 to 8.

First Embodiment

Figure 1:
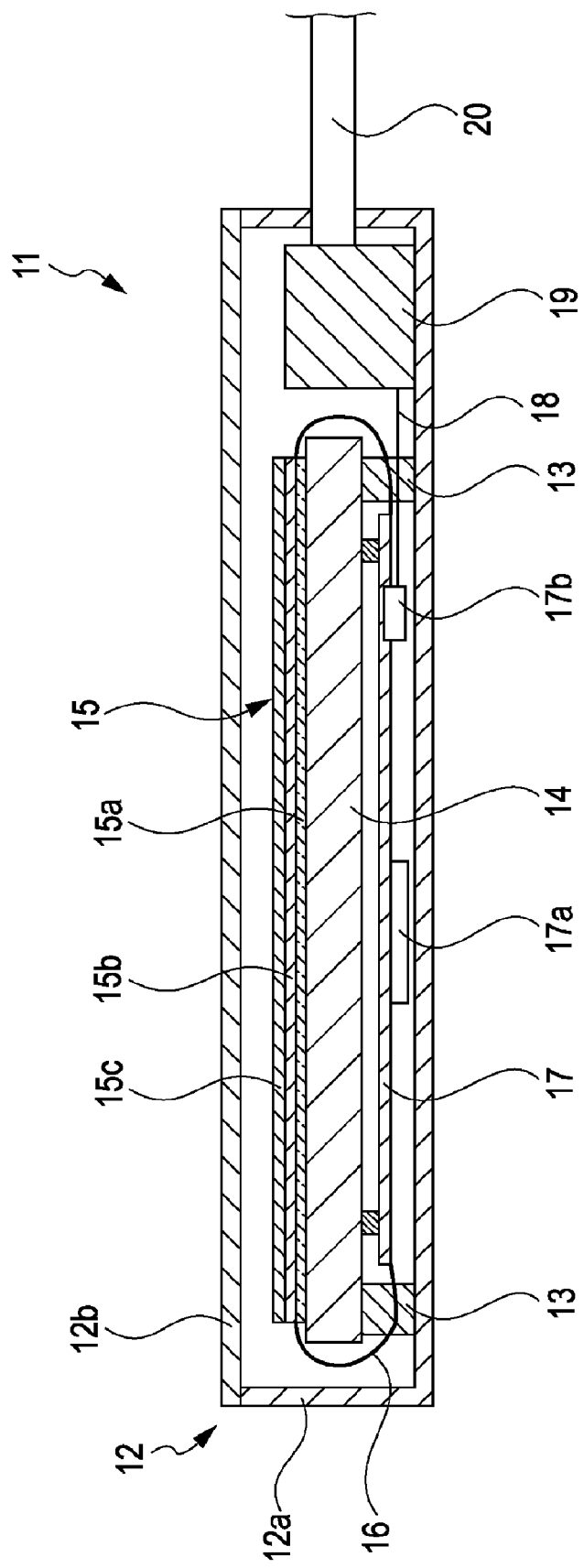
FIG. 1 is a perspective view of a radiographic imaging apparatus according to a first embodiment.

FIG. 1 is a cross-sectional view of an imaging device 11 serving as an imaging unit. This imaging device 11 is used alone as a cassette, or in combination with various mounts serving as a support unit. A radiation incident surface of a housing body 12a is covered with a housing cover 12b formed of a material having a high transmittance for radiation, thus defining a sealed housing 12. A metal base 14 is fixed in the housing body 12a with support portions 13 disposed therebetween. A radiographic-image detection panel 15 in which a substrate 15a, photoelectric conversion elements 15b, and a fluorescent plate 15c are stacked is provided on the base 14.

The substrate 15a is typically formed by a glass plate because a glass plate does not cause any chemical reaction to a semiconductor element, withstands the semiconductor process temperature, and meets the requirement of dimensional stability. The photoelectric conversion elements 15b are formed in a two-dimensional form on the substrate 15a by a semiconductor process. The fluorescent plate 15c is formed by a resin plate coated with a fluorescent material of a metal compound. The substrate 15a, the photoelectric conversion elements 15b, and the fluorescent plate 15c are combined by bonding.

The photoelectric conversion elements 15b are connected to a circuit board 17 via a flexible circuit board 16 connected to side faces thereof. The circuit board 17 is provided on a back side of the base 14, and has thereon electronic components 17a and 17b for processing photoelectrically converted electric signals. The circuit board 17 is connected to a relay electric circuit portion 19 via a cable 18, and is further connected to an external control unit (not shown) via a cable 20 so as to supply power and to transfer signals.

The imaging device 11 can take a radiographic image in combination with a radiation generation device 28 provided thereabove to emit radiation. When radiation emitted from the radiation generation device 28 passes through a subject and enters the imaging device 11, the fluorescent plate 15c of the radiographic-image detection panel 15 emits light. The photoelectric conversion elements 15b arranged in a two-dimensional manner convert the light into electric signals to obtain a digital image. Further, the digital image can be transferred via the cable 20 and be instantaneously observed on a monitor (not shown).

To read out charges from the radiographic-image detection panel 15, charges stored in a plurality of photoelectric conversion elements 15b in a column selected by a driving circuit (not shown) are released in the row direction, and are read by read-out circuits (not shown) provided corresponding to the rows. During such driving of the imaging device 11, the electronic components 17a and 17b generate heat with power consumption. Heat generated from the electronic components 17a and 17b increases the temperature in the imaging device 11, and is radiated into external air via through the housing 12.

Figure 2:
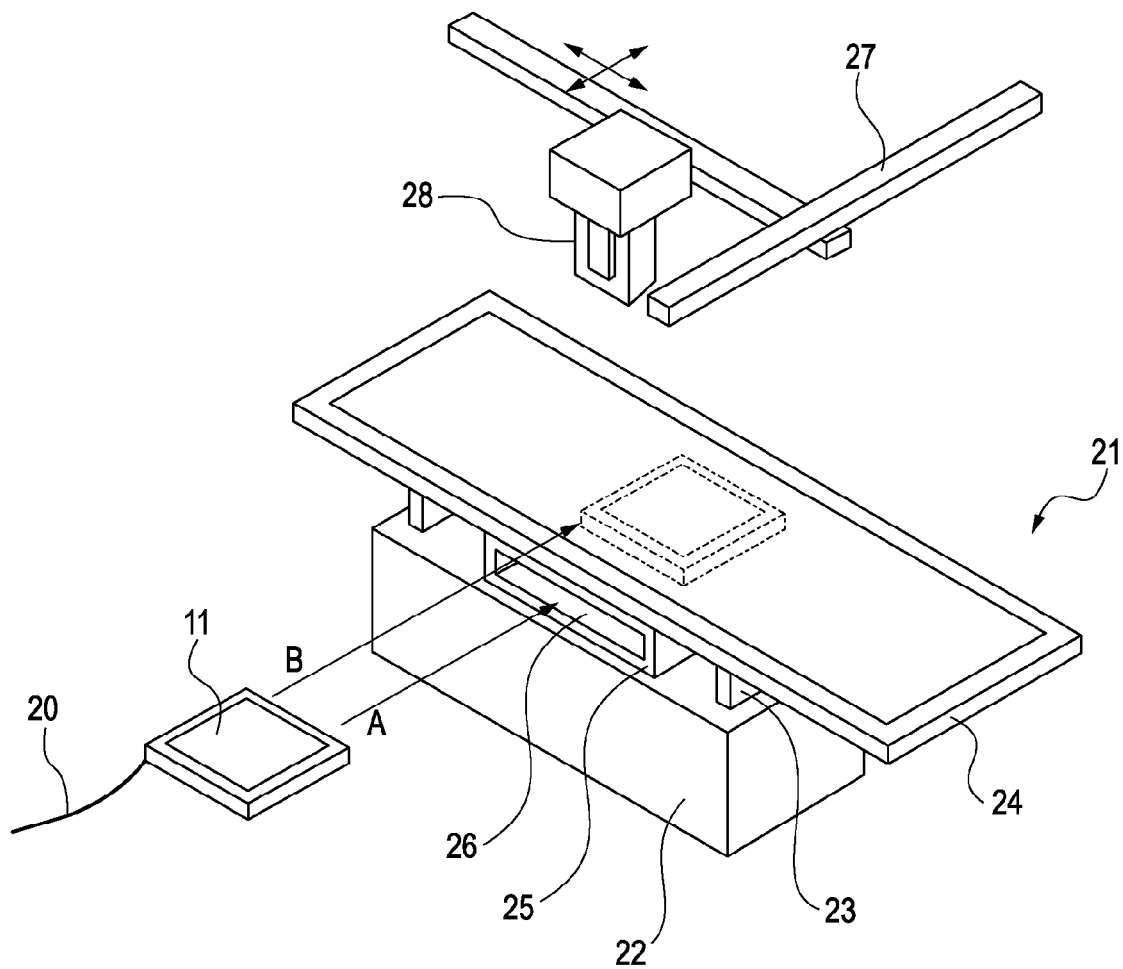
FIG. 2 is a perspective view of the radiographic imaging apparatus of the first embodiment.

FIG. 2 is a structural view showing a state in which the imaging device 11 is used in combination with an imaging table 21. The imaging table 21 is supported on a table body 22 with support portions 23 disposed therebetween in a manner such that a top plate 24 on which a subject is placed is movable in a horizontal plane. Between the table body 22 and the top plate 24, a storage section 25 serving as a support unit in which the imaging device 11 is mounted is provided. An aperture 26 through which the imaging device 11 is inserted is provided in a front surface of the storage section 25. The radiation generation device 28 for emitting radiation is provided above the imaging table 21, and is movable along a guide portion 27. A unit for supporting the imaging device 11 is referred to as a support unit.

The imaging device 11 can be set in the imaging table 21 by two methods, that is, a method of inserting the imaging device 11 in the storage section 25 in the direction of arrow A and a method of placing the imaging device 11 on the top plate 24 in the direction of arrow B.

In the former method in which the imaging device 11 is inserted in the storage section 25 in the direction of arrow A, the subject does not directly touch the imaging device 11, and therefore, can be easily aligned with the imaging device 11. In the latter method in which the imaging device 11 is placed on the top plate 24 in the direction of arrow B, the imaging device 11 has the flexibility of being able to be positioned in various postures.

When the imaging device 11 is mounted in the storage section 25, the relative position therebetween needs to be properly determined to precisely align the radiation generation device 28 and the imaging device 11.

Figure 3:
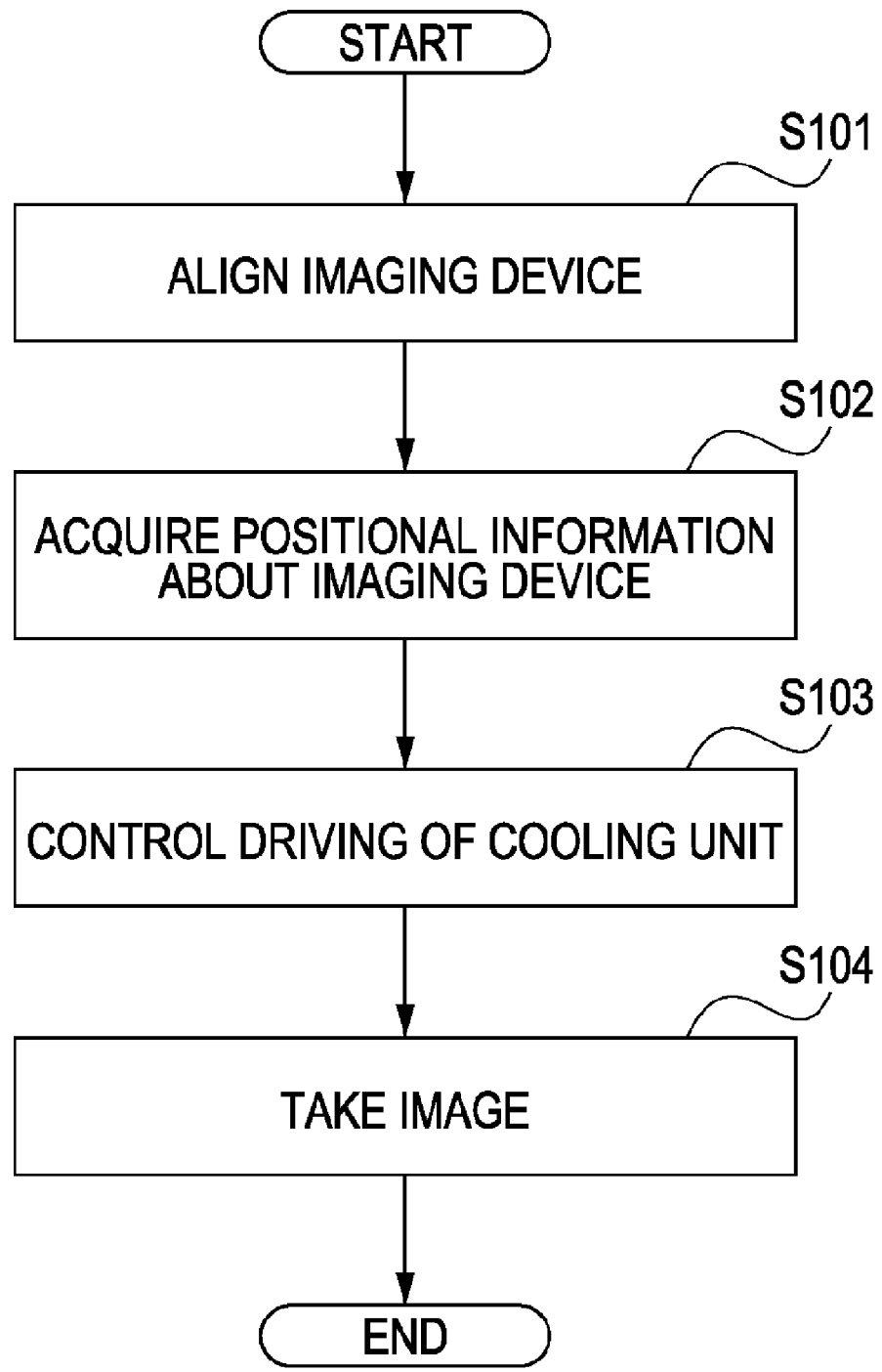
FIG. 3 is a flowchart showing a procedure performed in the first embodiment.

FIG. 3 is a flowchart showing a procedure performed in the first embodiment. The following description will be given according to the flow of the procedure.

Figure 4:
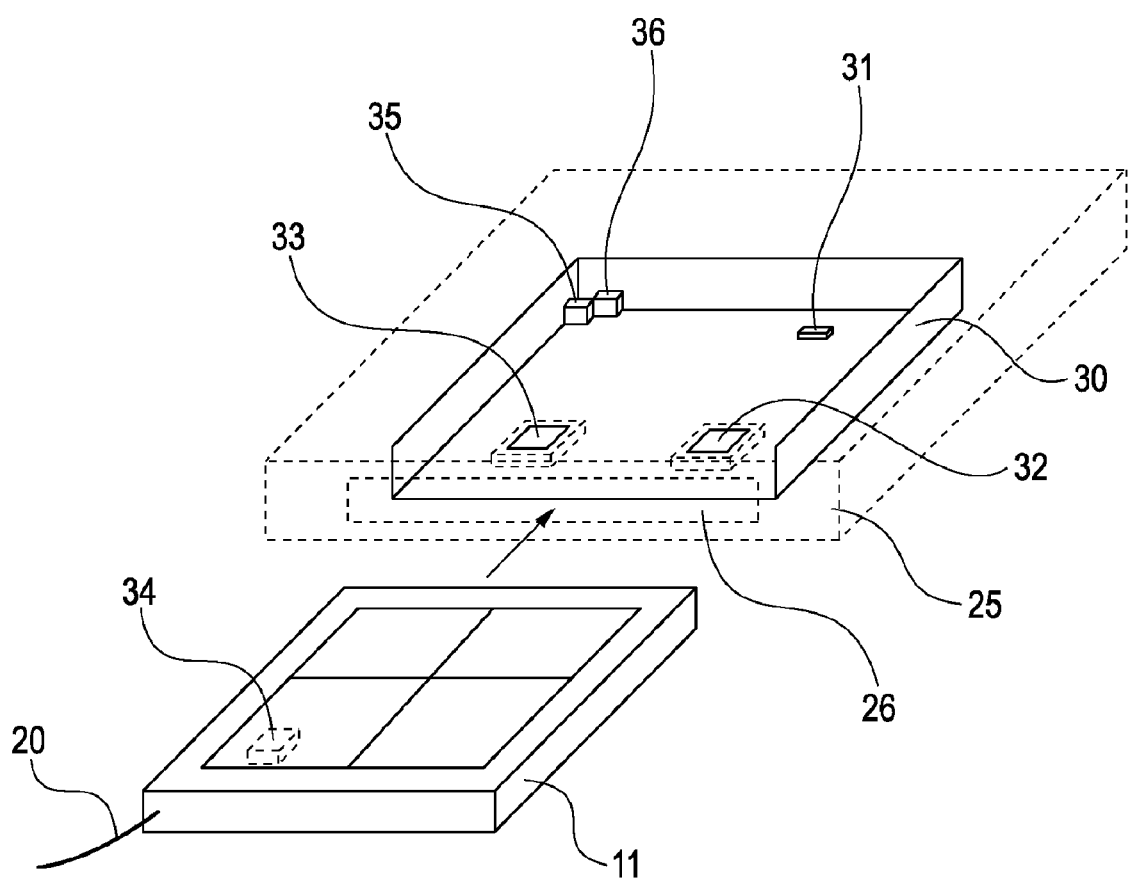
FIG. 4 is a structural view of a storage section in the first embodiment.

FIG. 4 shows the structure of the storage section 25. The storage section 25 and the aperture 26 for insertion are shown by broken lines to represent the internal structure. A support frame 30 is provided in the storage section 25. The support frame 30 has a bottom face provided in a plane perpendicular to the irradiation axis, and three side walls. The imaging device 11 is inserted into the storage section 25 from the front side of the plane of FIG. 4, and is pushed in until the leading end thereof comes into contact with the far wall. In this case, a latch member 31 catches a bottom face of the imaging device 11 to regulate insertion and removal (S101).

Figure 5A:
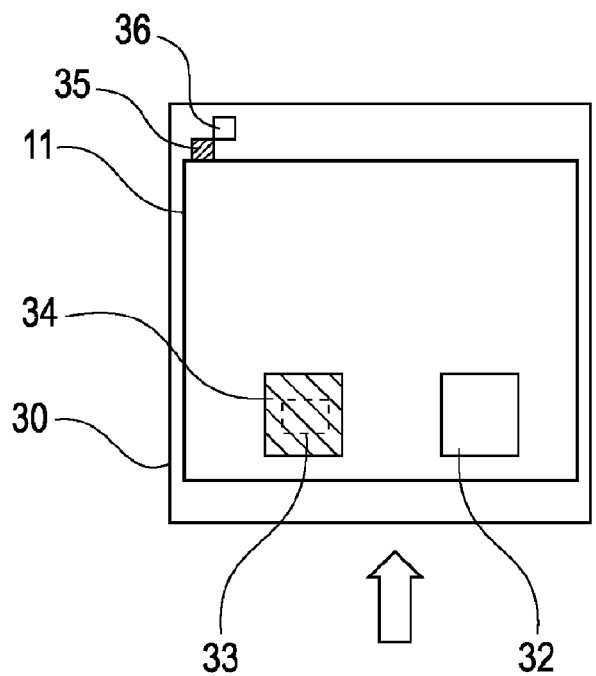
FIGS. 5A and 5B are explanatory views illustrating cooling portions and an imaging device.
Figure 5B:
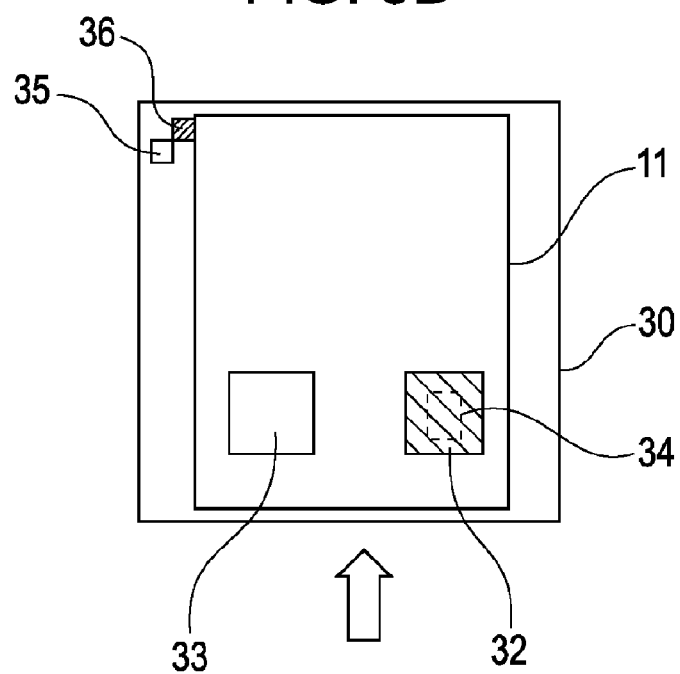

An image receiving area of the imaging device 11 for receiving radiation is generally defined in accordance with the size of existing radiographic films. Films are shaped like a rectangular having a size of, for example, 35×43 mm or 20×25 mm. For this reason, the imaging device 11 is used in landscape or portrait orientation according to a portion to be irradiated. FIGS. 5A and 5B show states in which the imaging device 11 is placed in landscape and portrait orientations in the support frame 30 of the storage section 25. At a corner of the support frame 30, two detectors 35 and 36 are provided to detect the orientation of the mounted imaging device 11 and to acquire information about at least one of the position and posture of the imaging device 11. When the imaging device 11 is mounted with its longitudinal direction coinciding with the horizontal direction, as shown in FIG. 5A, the detector 35 reacts. Conversely, when the imaging device 11 is mounted with in portrait orientation, as shown in FIG. 5B, the detector 36 reacts. The detectors 35 and 36 can be easily realized by, for example, microswitches or non-contact magnetic sensors.

Output signals from the detectors 35 and 36 are transmitted to an information acquisition unit (not shown) for acquiring information about at least one of the position and posture of the imaging device 11 (S102).

Also, cooling portions 32 and 33 that constitute a cooling unit are provided on the support frame 30. As described above, when the imaging device 11 is driven, heat is generated with power consumption of the electronic components. In particular, a regulator or the like causes local heat generation, and this makes in-plane temperature distribution nonuniform. Accordingly, when the imaging device 11 has a heat generating portion 34, the cooling unit is provided in the storage section 25 to locally cool the heat generating portion 34 and to thereby reduce nonuniformity of temperature distribution in the imaging device 11. The cooling unit in the first embodiment includes a plurality of cooling portions, such as fans or Peltier devices, for the purpose of forced cooling. The cooling unit is provided on the back side of the imaging device 11 in a manner such as to face the heat generating portion 34 when the imaging device 11 is mounted in the storage section 25. Since the imaging device 11 is mounted in two orientations, that is, landscape orientation and portrait orientation, the cooling portions 32 and 33 of the cooling unit are arranged at positions such as to face the heat generating portion 34. When the orientation of the mounted imaging device 11 is detected by the above-described detector 35 or 36, the cooling unit is selectively driven according to the detection result (S103). Driving of the cooling unit is controlled by the control unit.

When the imaging device 11 is mounted in landscape orientation, as shown in FIG. 5A, only the cooling portion 33 facing the heat generating portion 34 is driven. In contrast, when the imaging device 11 is loaded in portrait orientation, as shown in FIG. 5B, only the cooling portion 32 is driven. Driving is controlled under instructions from the external control unit.

By selectively controlling the driving of the cooling unit in accordance with the mount state of the imaging device 11, as described above, it is possible to reduce nonuniformity of the temperature distribution of the imaging device 11 by effective cooling while limiting power consumption.

Second Embodiment

Figure 6:
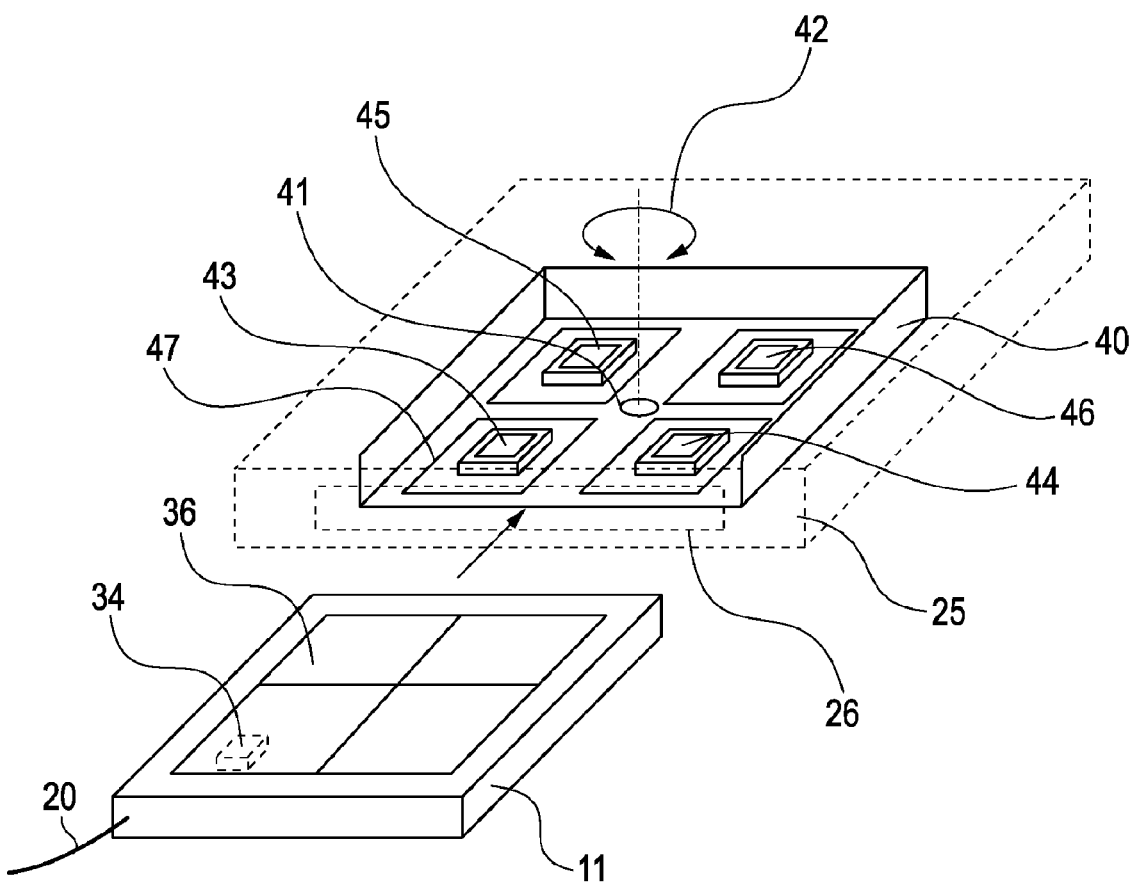
FIG. 6 is a structural view of a storage section according to a second embodiment.

FIG. 6 shows a structure of a storage section 25 serving as a support unit incorporated in an imaging table 21 similar to that adopted in the first embodiment. The same processes and structures as those in the first embodiment are denoted by the same reference numerals, and descriptions thereof are omitted.

In the first embodiment, to change the orientation of the mounted imaging device 11, it is necessary to take the imaging device 11 out of the storage section 25 and to mount the imaging device 11 again after changing the orientation. It is desirable to the operator that the orientation of the imaging device 11 can be changed more easily. Accordingly, the second embodiment adopts a function of changing the orientation of the imaging device 11 in the storage section 25.

The degree of temperature rise in the storage section 25 varies according to the radiation frequency at which radiation is applied to the imaging device 11. For this reason, in the second embodiment, a control unit controls driving of a cooling unit also in consideration of the radiation frequency.

Figure 7:
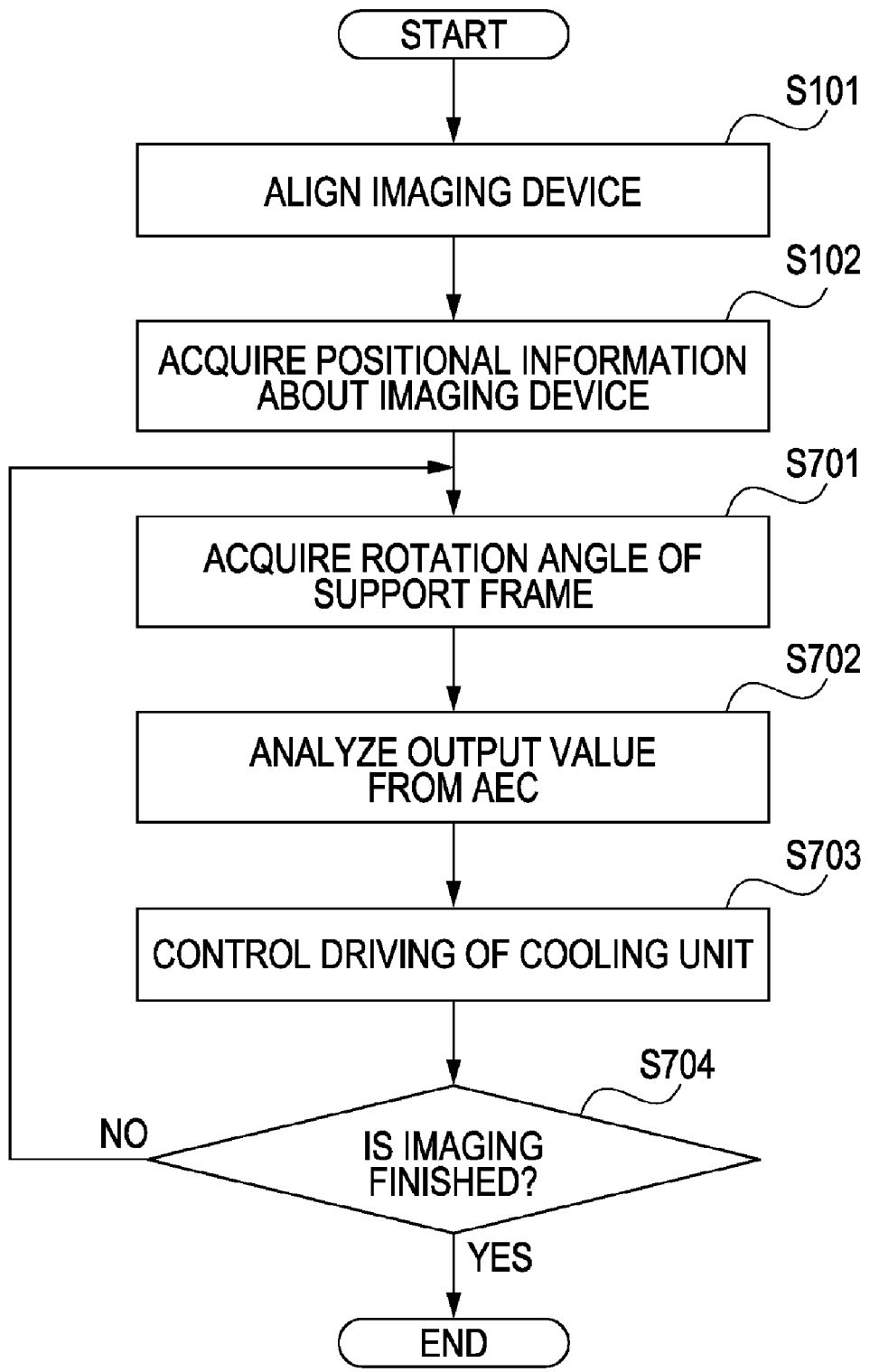
FIG. 7 is a flowchart showing a procedure performed in the second embodiment.

FIG. 7 is a flowchart showing a procedure performed in the second embodiment. The same processes as those adopted in the first embodiment are denoted by the same reference numerals, and descriptions thereof are omitted.

A support frame 40 is provided in a storage section 25 so as to hold an imaging device 11 and precisely maintain the position of the imaging device 11 relative to the storage section 25. The support frame 40 has a rotational bearing 41 on a bottom face, and is rotatable on an axis 42. The rotational bearing 41 also transmits the rotation angle of the support frame 40 in the form of signals to the control unit.

An AEC (Automatic Exposure Control) detector (not shown) serving as a detection unit for detecting the amount of radiation emitted from a radiation generation device 28 is incorporated in the imaging device 11. The AEC detector outputs an electric signal when the amount of received radiation exceeds a predetermined value. According to this electric signal, radiation from the radiation generation device 28 is stopped. The electric signal is also transmitted to the control unit.

The rotation axis 42 substantially coincides with the center of an image receiving area of the imaging device 11. Since the radiation axis coincides with the rotation axis 42, it does not deviate even during rotation, and the radiation generation device 28 and the imaging device 11 can therefore be aligned easily.

In other words, the imaging device 11 can rotate in a plane perpendicular to the radiation axis while maintaining the positional relationship between the imaging device 11 and the cooling unit.

When the imaging device 11 is mounted, it comes into contact with the far side and is held at that position, similarly to the first embodiment. The operator can switch the orientation of the imaging device 11 to a desired orientation with a position changing member provided on a control panel of an imaging table (not shown). Apertures 47 are provided in the bottom face of the support frame 40, and cooling portions 43 to 46 of the cooling unit are arranged corresponding to the apertures.

The control unit acquires the angle of rotation of the support frame 40 on the axis 42 (S701) in this case, and selects, from the cooling portions 43 to 46, a cooling portion to be used for cooling. Next, a calculation unit (not shown) calculates the imaging frequency of the imaging device 11 on the basis of an output signal from the AEC detector serving as the detection unit (S702). In this case, since the finish timing of irradiation can be obtained from the AEC detector, the radiation frequency per unit time can be calculated. Since the temperature in the storage section 25 increases as the radiation frequency increases, the control unit increases the output performance of any selected one of the cooling portions 43 to 46 as the radiation frequency calculated by the calculation unit increases (S703). Alternatively, the control unit increases the number of cooling portions to be driven as the radiation frequency calculated by the calculating unit increases (S703). Further, the control unit decreases the output performance of the selected cooling portion as the radiation frequency decreases. Alternatively, the control unit decreases the number of cooling portions to be driven as the radiation frequency calculated by the calculation unit decreases (S703). In this way, the control unit controls driving of the cooling unit until the imaging operation is completed.

The cooling unit serves to cool the back side of a mounted imaging device, similarly to the cooling unit adopted in the first embodiment. In a state shown in FIG. 6 in which the imaging device 11 is mounted, the cooling portion 43 is selectively driven to cool the adjacency of the heat generating portion 35 in the imaging device 11. When the support frame 40 rotates, the state of rotation is grasped, and a corresponding cooling portion is selectively driven. This makes the internal temperature of the imaging device 11 uniform, obtains stable image quality, and improves the operability of the imaging table. In addition, since the cooling performance can also be changed also in accordance with the imaging frequency, the internal temperature of the imaging device 11 can be stably made uniform.

Third Embodiment

Figure 8:
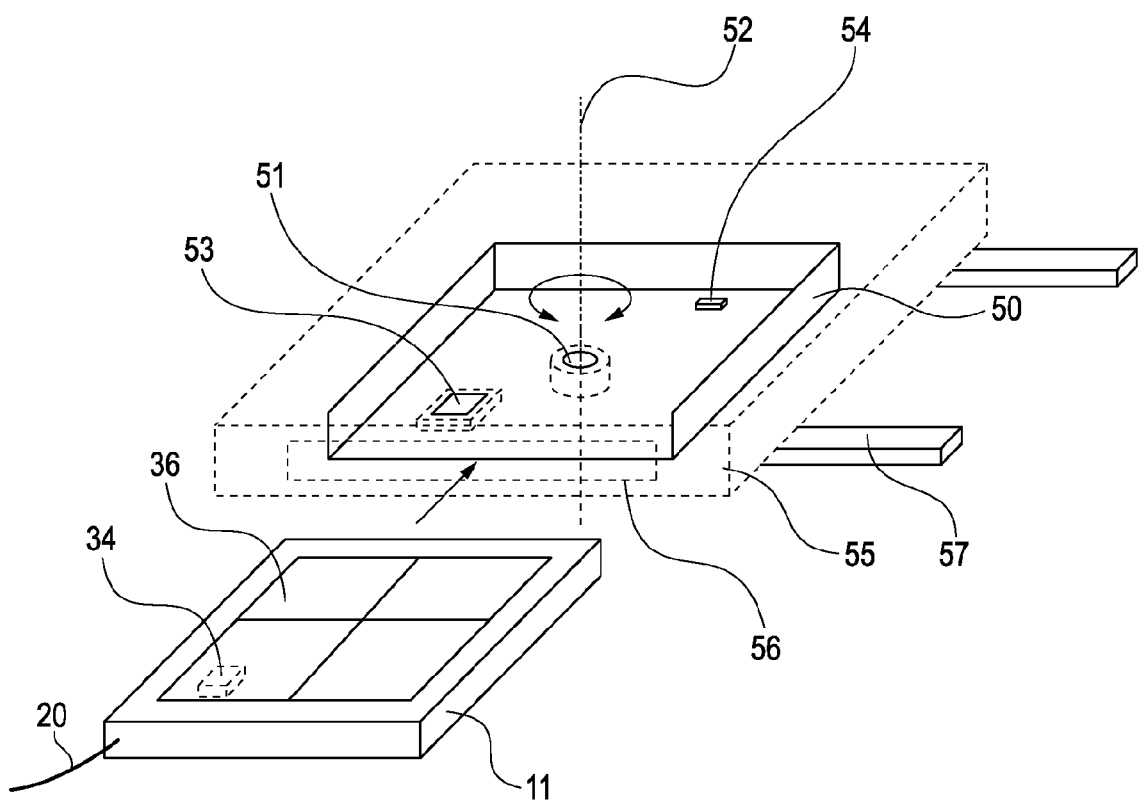
FIG. 8 is a structural view of a storage section according to a third embodiment.

FIG. 8 shows a structure of a storage section 55 serving as a support unit incorporated in an imaging table 21 according to a third embodiment serving as a modification of the first and second embodiments. The same processes and structures as those adopted in the first embodiment are denoted by the same reference numerals, and descriptions thereof are omitted.

The storage section 55 and an aperture 56 for insertion are shown by broken lines to represent the internal structure. Similarly to the first and second embodiments, a support frame 50 is provided in the storage section 55, and has a bottom face provided in a plane perpendicular to the radiation axis, and three side walls. An imaging device 11 is inserted from the front side of plane of FIG. 8, and is caught and held in position by the support frame 50.

The bottom face of the support frame 50 is provided with a bearing 51 at a rotation axis 52 parallel to the irradiation axis of radiation emitted from a radiation generation device 28, and is rotatable at an arbitrary angle. For example, to put a long portion, such as a femur, in an imaging area of the imaging device 11, the portion needs to be aligned in the diagonal direction. It is not enough to switch between the landscape and portrait orientations as in the first and second embodiments. When the diagonal line of the image receiving area of the imaging device 11 can point in the longitudinal direction of the imaging table, alignment with the subject can be performed easily. Further, the rotation axis 52 substantially coincides with the center of the image receiving area of the imaging device 11, similarly to the second embodiment. Since the radiation axis coincides with the rotation axis 52, it does not deviate even during rotation.

The storage section 55 itself is supported by guide members 57 so as to be movable in the longitudinal direction below a top plate 24. In this case, it is also possible to change the position of the imaging device 11 while maintaining a cooling unit in a stable state.

A cooling portion 53 is provided on the support frame 50 so as to locally cool a heat generating portion 34 in the imaging device 11 and to reduce nonuniformity of the distribution of the internal temperature of the imaging device 11. Even when rotated, the position of the cooling portion 53 relative to the imaging device 11 can be maintained. This structure eliminates the necessity of a plurality of cooling portions, and ensures cooling performance even during arbitrary rotation.

Fourth Embodiment

A fourth embodiment will now be described with reference to FIGS. 9 and 10. The same processes and structures as those adopted in the first embodiment are denoted by the same reference numerals, and descriptions thereof are omitted.

Figure 9:
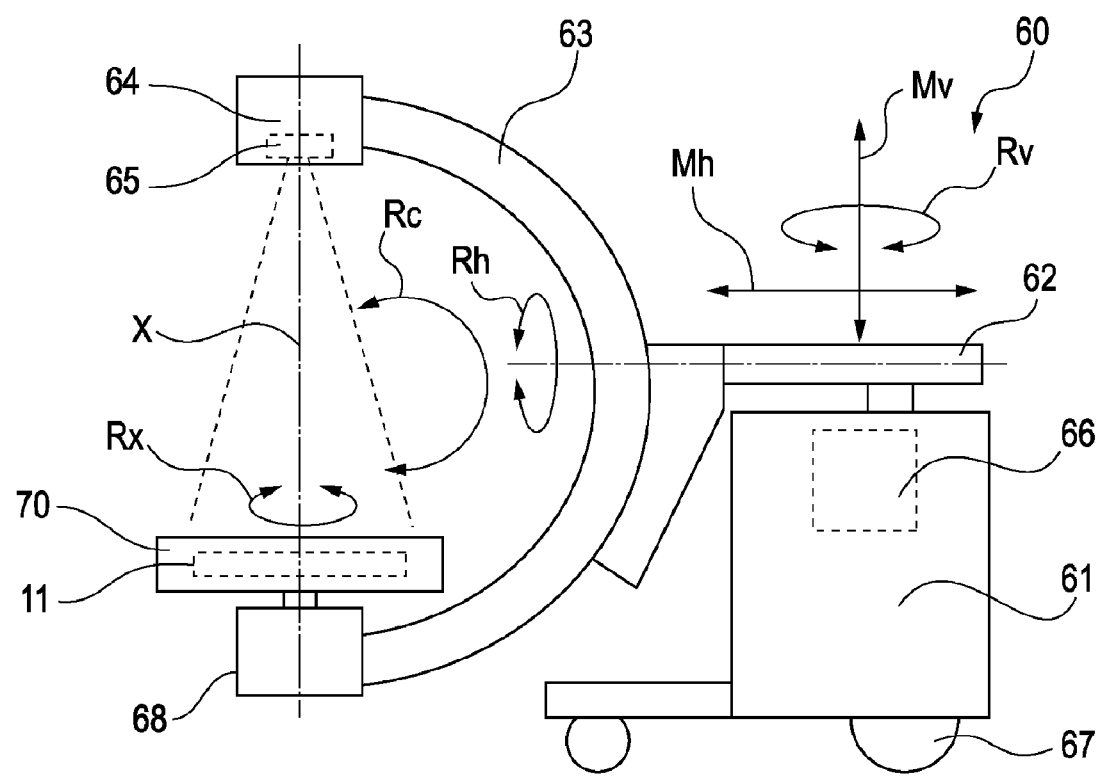
FIG. 9 is a front view of a radiographic imaging apparatus according to a fourth embodiment.
Figure 10:
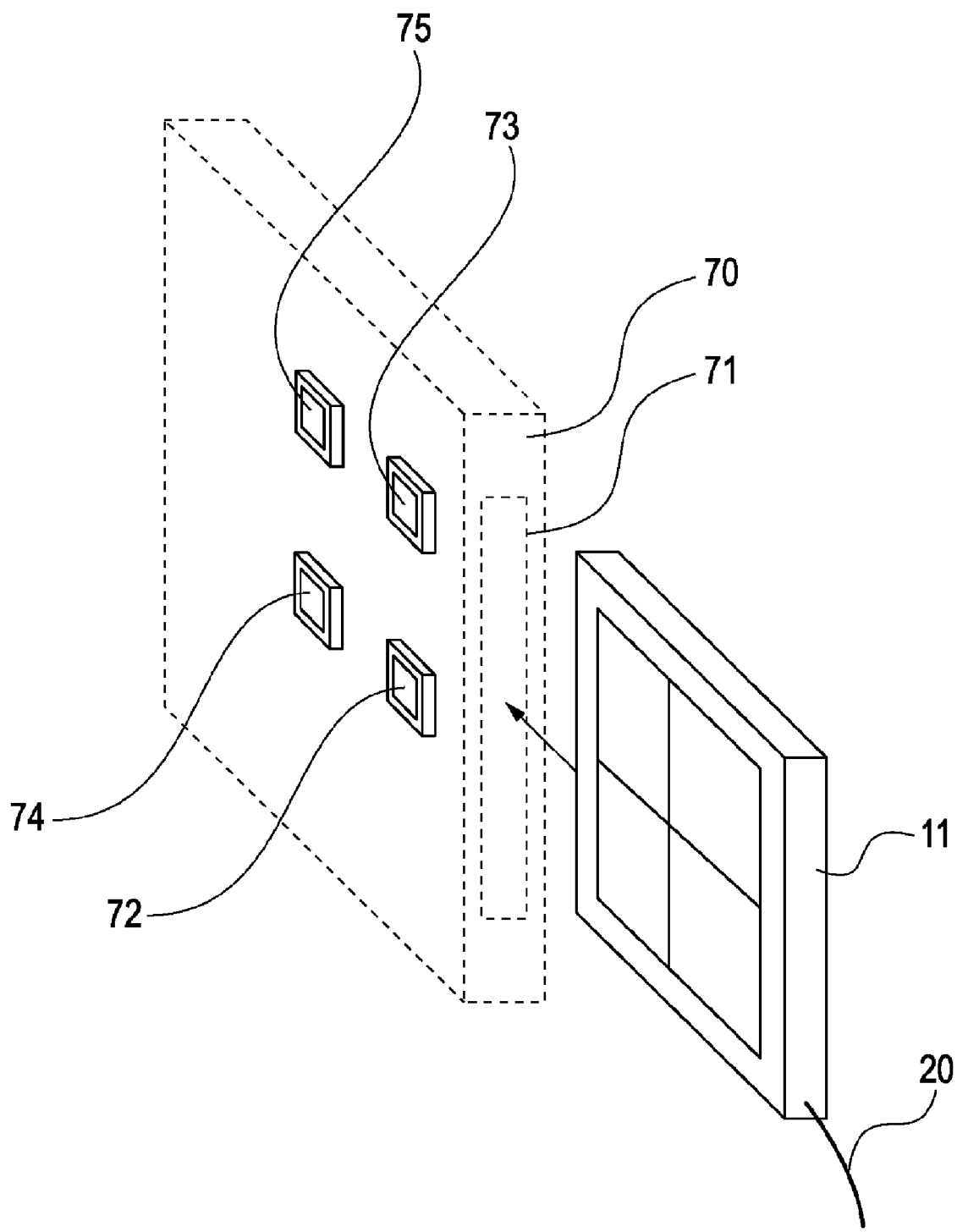
FIG. 10 is a structural view of a storage section in the fourth embodiment.
Figure 11:
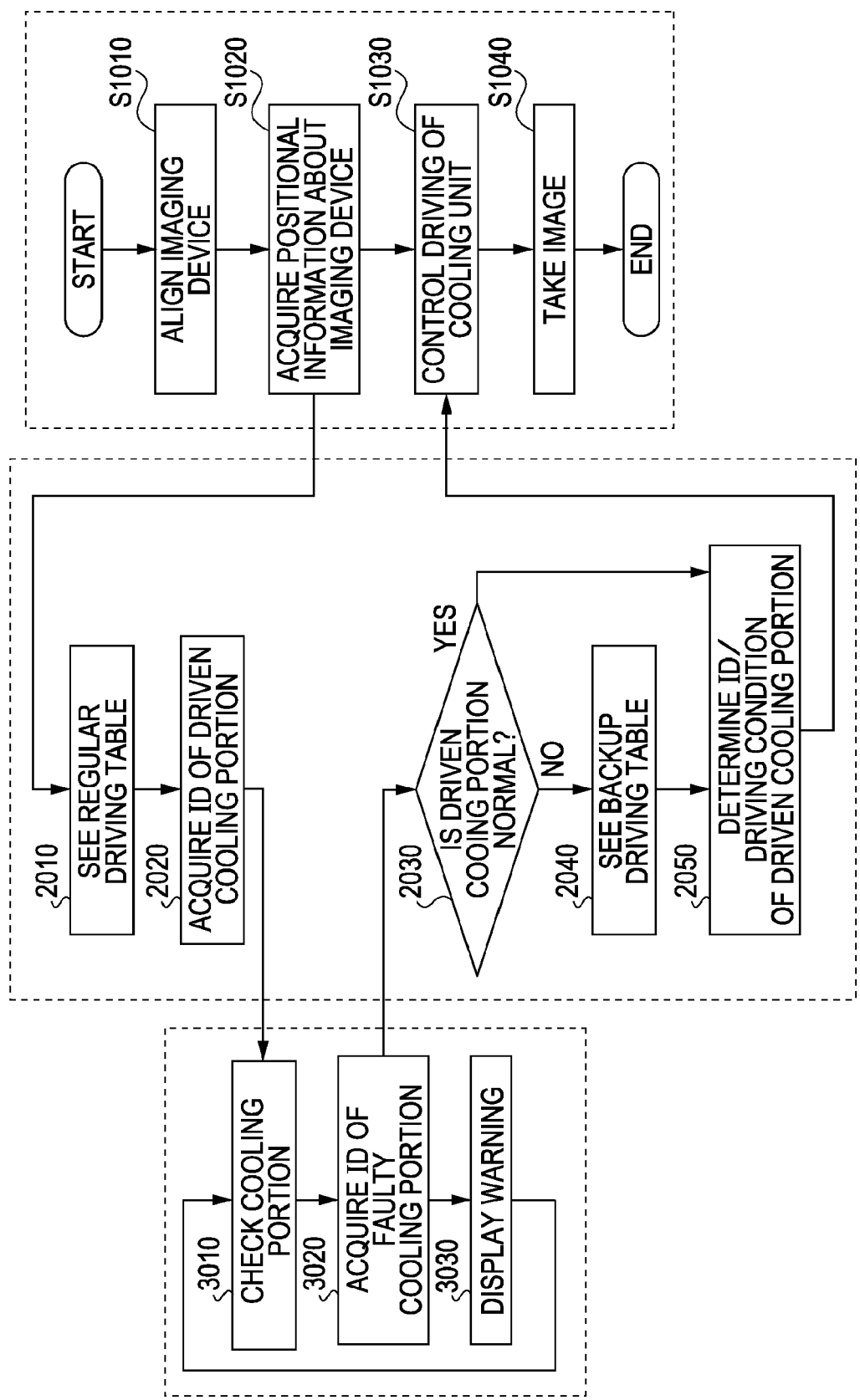
FIG. 11 is a flowchart showing a procedure performed in the fourth embodiment.
Figure 12:
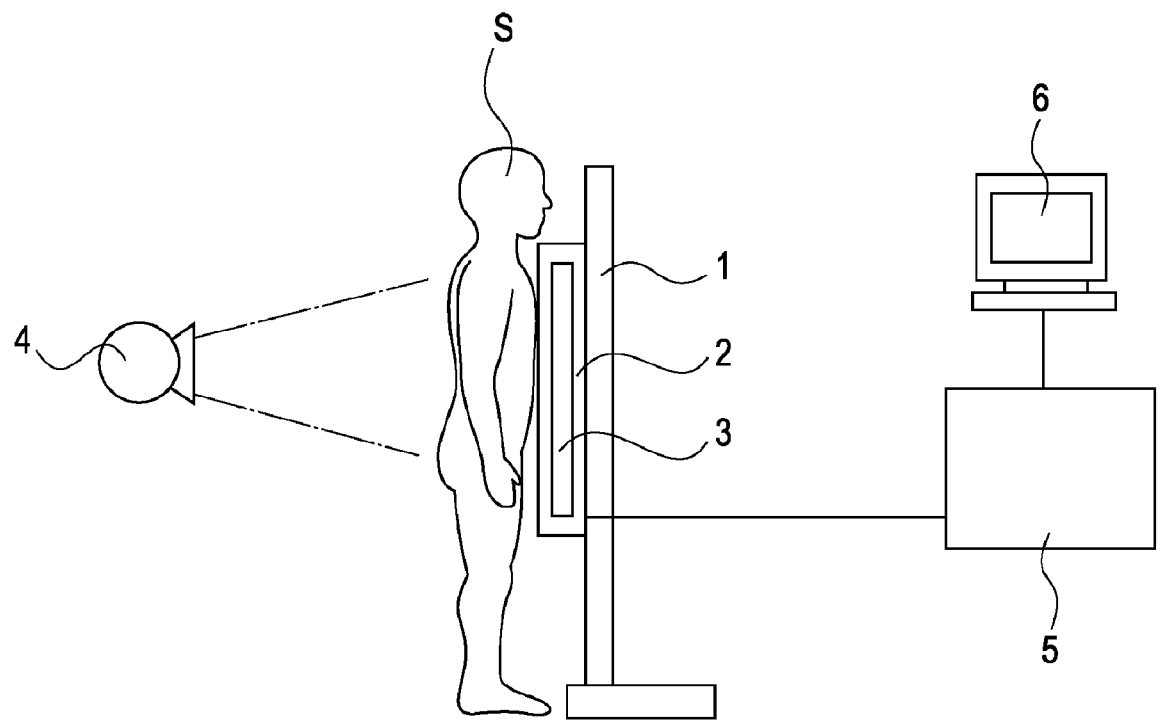
FIG. 12 is a structural view of a radiographic imaging system of the related art.

FIG. 9 shows a storage section 70 serving as a support unit for supporting an imaging device, and FIG. 10 shows cooling portions 72 to 75 of a cooling unit mounted in the storage section 70. FIG. 11 is a flowchart showing a procedure performed in the fourth embodiment. The same processes and structures as those adopted in the first embodiment are denoted by the same reference numerals, and descriptions thereof are omitted.

An imaging device 11 is used in combination with various support mechanisms. As a typical example, FIG. 9 shows a system in which the imaging device 11 is combined with a mobile C-arm device 60. The mobile C-arm device 60 includes a horizontal shaft 62 supported by a main body 61 so as to be movable up and down, and a C-shaped arm member 63 provided at a leading end of the horizontal shaft 62. These components can make rotations (shown by arrows Rc, Rh, and Rv in FIG. 9) and movements (shown by arrows Mh and Mv). A radiation generating section 64 and the storage section 70 are respectively provided at opposite ends of the C-arm member 63 in a manner such as to face each other. The storage section 70 serves as a support unit for holding the imaging device 11 that receives a radiographic image. Imaging is performed in a state in which the subject is between the radiation generating section 64 and the storage section 70. A control device 66 provided in the main body 61 includes a control unit. The storage section 70 permits at least one of translational and rotational movements of the imaging device 11 in a plane orthogonal to the irradiation axis of radiation emitted from the radiation generating section 64.

The radiation generating section 64 and the imaging device 11 are supported with a constant distance therebetween. An effective imaging area of the imaging device 11 is rectangular, unlike a circular area of the II type. Hence, depending on a portion to be irradiated, position adjustment is necessary to align a desired area with the effective imaging area. While positioning can be performed by the above-described moving mechanism of the C-arm device 60, fine alignment is difficult.

For alignment with high operability, it is preferable to rotate the imaging device 11 in an irradiation surface. For that purpose, as shown in FIG. 9, a rotation mechanism is provided to rotate the storage section 70 in a direction of arrow Rx on almost the center (X-axis) of the effective imaging area. The above-described mechanisms allow the imaging device 11 to be used in a position at an arbitrary angle with respect to the subject (S1010).

Since the posture of the imaging device 11 is arbitrary in the fourth embodiment, it has an influence on the distribution of the internal temperature. For example, when a heat generating portion is provided in a lower part in the weight direction, heat is convected in the imaging device 11. Conversely, when the heat generating portion is in an upper part, the temperature increases near the heat generating portion. Consequently, the cooling performance differs according to the posture of the imaging device 11.

FIG. 10 shows a state in which the storage section 70 is held in a vertical position in the gravity direction. One surface of the storage section 70 has an aperture 71 through which the imaging device 11 is inserted. Cooling portions 72 to 75 of a cooling unit are provided in the storage section 70 in a manner such as to face the back side of the imaging device 11. These cooling portions 72 to 75 are formed by, for example, air blowing fans for air cooling, and the air volume and air blowing direction thereof can be electrically switched under the control of the control unit. Further, ID numbers are respectively assigned to the cooling portions 72 to 75.

The control unit stores, in a storage unit, a regular driving table showing position/posture information about the imaging device 11 and the driving condition for the cooling unit as a first table. For example, position/posture information about the imaging device 11 and ID numbers of the cooling portions 72 to 75 to be driven are correlated with the regular driving table. Also, the air speed and air blowing direction are correlated as driving methods for the cooling portions 72 to 75. Since driving according to the first table may become impossible because of failure, a second table is stored in the storage unit beforehand for each faulty cooling portion.

The C-arm device 60 includes a detection unit for detecting the position and posture of the imaging device 11. The detection unit can be realized by monitoring the states of moving mechanisms in the C-arm device 60 and calculating the posture of the imaging device 11, or mounting a detector, such as a gyroscope, in the storage section 70. An output signal from the detection unit is transmitted to the control unit (S1020).

The control unit acquires an ID number of a cooling portion to be driven, according to the output signal from the detection unit and the first table (S2010, S2020).

The control unit determines whether or not the cooling portion corresponding to the ID number is faulty (S3010). When a faulty cooling portion is detected, the control unit acquires the ID number of the cooling portion (S3020). Then, the control unit informs the operator of the fact that the cooling portion is faulty, for example, using a display unit (not shown) (S3030).

The control unit determines whether or not any of the cooling portions 72 to 75 is faulty (S2030). When a faulty cooling portion is detected, the control unit refers to the second table (S2040). When a faulty cooling portion is not found, the control unit refers to the first table. Then, the driving unit determines the ID number of the driving portion (sometimes referred to as a cooling device) to be driven and the driving condition (S2050). According to these, the control unit performs imaging while controlling the driving of the cooling device (S1040).

When the imaging device 11 is placed in a position vertical in the gravity direction, as shown in FIG. 10, an upper part of the interior of the imaging device 11 in the gravity direction is heated by a natural convection current. To make the distribution of the internal temperature of the imaging device 11 uniform, it is preferable to further cool the upper part. Accordingly, the air blowing fans 73 and 75, which are arranged in the upper part in the gravity direction, are driven on the intake side by the control unit so as to blow external air onto the back side of the imaging device 11, and the lower air blowing fans 72 and 74 are driven on the air exhaust side, whereby the air flow can be controlled.

When the posture of the storage section 70 changes from the state shown in FIG. 10, the control unit switches at least one of the air blowing direction and the air volume of the air blowing fans according to the position/posture information.

The control unit receives the output signal from the detection unit, and can acquire information about the position and posture of the imaging device 11.

While the imaging apparatus can be entirely cooled by increasing the power of the cooling unit, power consumption can be reduced by controlling the driving of the cooling unit, as described above. In the mobile device, such as the C-arm device, battery power consumption can be reduced.

While the present invention has been described with reference to the preferred embodiments, it is to be understood that the invention is not limited to these embodiments. Various modifications and alterations can be possible without within the scope of the invention. In particular, while the mount used in combination is not limited to the imaging table and the mobile C-arm device, for example, an upright stand or a universal stand can be similarly used.

This application claims priority from Japanese Patent Application No. 2008-224648 (2008/09/02) filed on Sep. 2, 2008, the entire contents of which are hereby incorporated by reference herein.

What is claimed is:

1. A radiographic imaging apparatus comprising:
    an imaging unit configured to convert radiation into an electric signal;
    a support unit configured to support the imaging unit;
    a cooling unit provided in the support unit, the cooling unit cooling the imaging unit;
    an information acquisition unit configured to acquire information about at least one of a position and a posture of the imaging unit; and
    a control unit configured to control driving of the cooling unit according to the acquired information.

2. The radiographic imaging apparatus according to claim 1, further comprising:
    a detection unit configured to detect an amount of the radiation; and
    a calculation unit configured to calculate a radiation frequency of the radiation on the basis of an output signal from the detection unit,
    wherein the control unit controls driving of the cooling unit according to the radiation frequency calculated by the calculation unit and the information acquired by the information acquisition unit.

3. The radiographic imaging apparatus according to claim 2,
    wherein the cooling unit includes a plurality of cooling portions, and
    wherein the control unit increases the number or output of the cooling portions to be driven as the radiation frequency calculated by the calculation unit increases.

4. The radiographic imaging apparatus according to claim 1,
    wherein the support unit permits at least one of translational and rotational movements of the imaging unit in a plane orthogonal to an radiation axis of the radiation while maintaining a relative position between the imaging unit and the cooling unit.

5. The radiographic imaging apparatus according to claim 1,
    wherein the cooling unit includes a plurality of cooling portions, and
    wherein the control unit selects any of the cooling portions to be driven according to the acquired information.

6. The radiographic imaging apparatus according to claim 1,
    wherein the cooling unit includes an air blowing fan, and
    wherein the control unit changes an air blowing direction of the air blowing fan according to the acquired information.

7. The radiographic imaging apparatus according to claim 1, wherein the cooling unit is located on a back surface of the imaging unit opposite a radiation incident surface.

8. The radiographic imaging apparatus according to claim 1,
wherein the cooling unit includes a plurality of cooling portions,
wherein the radiographic imaging apparatus further includes a storage unit configured to store, as a first table, the posture of the imaging unit and a driving condition for the cooling unit and to store, as a second table, the driving condition for the cooling unit corresponding to each faulty cooling portion, and
wherein the control unit detects whether or not the cooling portions are faulty, drives the cooling unit according to the first table when the cooling portions are not faulty, and drives the cooling unit according to the second table when a faulty cooling portion is detected.

9. The radiographic imaging apparatus according to claim 1, wherein the support unit is configured to support the imaging unit detachably.

10. An imaging method for a radiographic imaging apparatus including a cooling unit configured to cool an imaging unit that converts radiation into an electrical signal, the imaging method comprising the steps of:
acquiring information about at least one of a position and a posture of the imaging unit; and
controlling driving of the cooling unit according to the acquired information.

11. A radiographic imaging apparatus comprising: a cooling unit configured to cool an imaging unit that converts radiation into an electrical signal; an information acquisition unit configured to acquire information about at least one of a position and a posture of the imaging unit; and a control unit configured to control driving of the cooling unit according to the acquired information.

* * * * *